US006255502B1

(12) United States Patent
Penkler et al.

(10) Patent No.: US 6,255,502 B1
(45) Date of Patent: Jul. 3, 2001

(54) PHARMACEUTICAL COMPOSITION CONTAINING ACID ADDITION SALT OF BASIC DRUG

(75) Inventors: Lawrence John Penkler, Port Elizabeth; Luéta-Ann De Kock, Johannesburg; Darryl Vanstone Whittaker, Port Elizabeth, all of (ZA)

(73) Assignee: Farmarc Nederland B.V., Amersterdam (NL)

( * ) Notice: Subject to any disclaimer, the term of this patent is extended or adjusted under 35 U.S.C. 154(b) by 0 days.

(21) Appl. No.: 09/225,470

(22) PCT Filed: Jul. 11, 1997

(86) PCT No.: PCT/GB97/01873

§ 371 Date: Apr. 19, 1999

§ 102(e) Date: Apr. 19, 1999

(87) PCT Pub. No.: WO98/02187

PCT Pub. Date: Jan. 22, 1998

(30) Foreign Application Priority Data

Jul. 11, 1996 (ZA) .................................................. 96/5889

(51) Int. Cl.[7] ...................................................... C07J 9/00
(52) U.S. Cl. ..................... 552/549; 552/550; 554/156; 530/847; 514/177; 514/784; 514/946; 514/947; 424/550; 424/551; 424/553
(58) Field of Search .......................... 554/156; 514/784, 514/946, 947, 177; 424/550, 551, 553; 500/847; 552/549, 550

(56) References Cited

U.S. PATENT DOCUMENTS 4,722,941  2/1988  Eckert et al. ..................... 514/784

FOREIGN PATENT DOCUMENTS 0 463 653   1/1992   (EP) ............................. A61K/47/48
WO 94/16733  8/1994   (WO) ............................ A61K/47/48
WO 96/33742  10/1996  (WO) ............................ A61K/47/00

OTHER PUBLICATIONS

English Abstracts: JP 9278651; JP 9136835; JP 9136834; JP 9136828; JP 9104623; JP 9030965 and JP 8225448, (No date).
Chien, Y.W. ed., Novel Drug Deliver Systems, 2nd Edition, Marcel Dekker, 1992 pp. 183–188, 244–249.
Walker et al, Advanced Drug Delivery Reviews, 18(1996) pp. 295–301.
Lindmark et al, The Journal of Pharmacology and Experimental Therapeutics, vol. 275, No. 2, (1995), pp. 958–964.
Yamamoto et al, International Journal of Pharmaceutics, 93 (1993), pp. 91–99.
Tomita et al, Pharmaceutical Research, vol. 5, No. 6 (1988), pp. 341–346.

Mishima et al, J. Pharmacobio–Dyn., 10 (1987), pp. 624–631.
Aungst et al, Pharmaceutical Research, vol. 9, No.11 (1992), pp. 1507–1509.
Ogiso et al, Journal of Pharmaceutical Sciences, vol. 79, No. 2 (Dec. 1990).
Ogiso et al, Chem. Pharm. Bull., 39(10), pp. 2657–2661 (1991).
Green et al, Pharmaceutical Research, vol. 6, No. 7 (1989), pp. 628–632.
Jashnani et al, Journal of Pharmaceutical Sciences, vol. 82, No. 6 (Jun. 1993), pp. 613–616.
Loftsson et al, International Journal of Pharmaceutics, 115 (1995), pp. 255–258.
Vollmer et al, International Journal of Pharmaceutics, 99 (1993), pp. 51–58.
Legendre et al, European Journal of Pharmaceutical Sciences, 3 (1995), pp. 311–322.
Vollmer et al, J. Pharm. Pharmacol., vol. 46 (1994), pp. 19–22.
Merkus et al, Pharmaceutical Research, vol. 8, No. 5 (1991), pp. 588–592.
Shao et al, Pharmaceutical Research, vol. 9, No. 9 (1992), pp. 1157–1163.
Salehian et al, Journal of Clinical Endoerinology and Metabolism, vol. 80, No. 12, pp. 3567–3575., (No date).
Gill et al, European Journal of Pharmaceutical Sciences, vol. 1 (1994), pp. 229–236.
Szejtli, Cyclodextrin technology, Kluwer Academic Press, (1988), pp. 79–155.
Szejtli et al, Cyclodextrins in Pharmacy, Kluwer Academic Press, pp. 19–32, (No date).
Stella et al, Pharmaceutical Research, vol. 12, No. 9 (1995) S205.
Jashnani et al, J. Pharm. Sci., 82(6):13–24 (1996).
Nash et al, Skin Pharmacol., 5(3):160–170 (1992).
Elyan et al, J. Pharm. Sci., 85(1):101–105 (1996).
de Vries et al, Crit. Rev. Drug Carrier Systems, 8(3):290–298 (1991).

*Primary Examiner*—Deborah D. Carr
(74) *Attorney, Agent, or Firm*—Pillsbury Winthrop LLP

(57) ABSTRACT

A pharmaceutical composition contains an acid addition salt of a basic drug and a fatty acid or bile acid. The acid addition salts thus formed exhibit enhanced transmucosal and transdermal penetration of the basic drug. The acid addition salts, an inclusion complex containing said salts and a use of said salts are also disclosed.

13 Claims, No Drawings

PHARMACEUTICAL COMPOSITION CONTAINING ACID ADDITION SALT OF BASIC DRUG

This application is a 371 of PCT/GB97/01873 filed Jul. 11, 1997.

BACKGROUND OF THE INVENTION

This invention relates to a pharmaceutical composition formulated for transdermal or transmucosal delivery which contains as an active ingredient an acid addition salt of a basic drug and a fatty acid or bile acid, and to certain novel acid addition salts of basic drugs and fatty acids or bile acids.

The oral route of drug delivery is well established as the most preferred route of drug administration. However, when administered by the oral route a drug enters the gastrointestinal tract where many therapeutic agents are subjected to extensive presystemic elimination by gastrointestinal degradation and/or hepatic metabolism resulting in erratic or poor bioavailability. Further disadvantages of the oral route are difficulty in swallowing medications especially by the elderly or in paediatrics, or in the presence of nausea and vomiting.

Delivery of drugs via the oral, nasal, ocular, rectal or vaginal mucosae or via the skin, offers a means of avoiding the disadvantages of the oral route as the drug reaches the systemic circulation directly. The mucosal route of drug delivery is a useful alternative to parenteral delivery where rapid therapeutic effect is desired. The transermal route is advantageous for sustained release of active ingredients.

There are several methods known in the art to deliver drugs to the oral and nasal mucosae [see Chien, Y W ed. Novel Drug Delivery Systems, 2nd Edition, Marcel Dekker 1992, pp 183–188, 244–249]. These include buccal and sublingual tablets or lozenges, adhesive patches, gels, solutions or sprays (powder, liquid or aerosol) for the oral cavity and solutions or sprays (powder, liquid or aerosol) for the nasal cavity. Suppositories and pessaries are well known galenical forms for rectal and vaginal delivery, and sterile solutions, suspensions and ointments are similarly well established forms for ocular delivery [The Pharmaceutical Codex 12th Edition, The Pharmaceutical Press; Remington's Pharmaceutical Sciences 18th Edition, Mack Publishing Company]. Transdermal drug delivery has been extensively reviewed [Osborne, D W and Amann, A. Topical Drug Delivery Formulations, Marcel Dekker Inc.].

Relatively few drugs are currently administered via the mucosal and dermal routes due to problems associated with poor transport of the drugs across mucosal or dermal membranes. A given drug will partition between the lipid phase and the aqueous phase of biological membranes according to the lipophile/hydrophile balance of the drug molecule. According to pH partition theory, the permeation of an ionisable substance through biological membranes is dependent on the concentration of the unionised species. Basic drugs, depending on their pKa, are generally ionized to varying extents at the pH of the mucosal surface, resulting in poor transmembrane permeation.

The absorption of drugs from biological membranes may be enhanced by (i) increasing drug solubility, (ii) pH modification to favour the unionized form of the drug, (iii) addition of bioadhesive agents to improve contact between the delivery system and the membrane and (iv) incorporation of so-called penetration enhancers.

There are a number of penetration enhancers known to influence the permeability of drugs across biological membranes [for a recent review see Walker, R B and Smith, E W Advanced Drug Delivery Reviews 1996, 18, 295–301].

The mechanism by which sodium salts of medium chain fatty acids ($C_6$, $C_8$, $C_{10}$ and $C_{12}$) enhance the absorption of hydrophilic drugs across intestinal mucosa has been studied [Lindmark, T et al, J. Pharmacol. Exp. Ther. 1995, 275(2), 958–964.].

Oral absorption of antibiotics in U.S. Pat. No. 5,318,781 to Hoffmann-La Roche is claimed to be enhanced by use of salts (e.g sodium) of capric or caprylic acids together with an anionic surfactant.

Transdermal formulations containing absorption accelerators teaching the use of lauric acid diethanolamide salt is claimed in JP 05185371 to Sekisui Chemical Company Limited.

The effects of sodium salts of bile acids, caprylic or capric acids as nasal drug absorption promoters have been reported. [Yamamoto, A et al Int. J. Pharm. 1993, 93(1–3), 91–99.].

Colonic absorption of cefmetazole and inulin are reported to be increased by the use of sodium caprate, sodium laurate, and mixed micelles composed of sodium oleate and sodium taurocholate [Tomita, M. et al, Pharm. Res. 1988, 5(6), 341–346.].

The promoting effect of sodium caprylate, sodium caprate and sodium laurate on rat nasal absorption of insulin has been reported [Mishima, M et al, J. Pharmacobio-Dyn 1987, 10(11), 624–631.].

WO 9524197 to Sekisui Chemical Company Limited, Japan; Dainippon Pharmaceutical Company Limited teaches a percutaneously absorbable plaster composed of a support and, formed on one side thereof, a pressure-sensitive adhesive layer comprising a pressure-sensitive adhesive, a drug and a percutaneous absorption accelerator.

Skin penetration enhancement using free base and acid addition salt combinations of active agents are described in EP 321870 to Theratech Inc. Compositions for topical application were prepared containing active pharmaceutical permeants capable of existing in both free base and acid addition salt form. The acids used included HCl, tartrate, sulphate, HBr, mesylate and maleate.

A fatty acid salt of propranolol as an alternative to polymeric formulations was investigated for possible use in sustained-release oral formulations and evaluated in dogs. An increase in bioavailability was observed after propranolol laurate was administered. [Aungst, B J; Hussain, M A, Pharm. Res. 1992,9(11), 1507–9.].

In an article in J. Pharm. Sci (1990), 79(12), 1065–1071 by T Ogiso and M Shintani the effects of a series of fatty acids including lauric acid and myristic acid on the percutaneous absorption of propranolol was examined. The results indicate that a significant proportion of propranolol will penetrate across the stratum corneum by forming a complex with a fatty acid, and that the complex will dissociate to each component in the interface between the corneum and a viable epidermis, where propranolol partitions into this water-rich tissue.

In an article in Chem. Pharm. Bull. (1991), 39 (10), 2657–2661 by T Ogiso et al, there is reported that propranolol suppositories with lauric acid at various molar ratios were administered to the rat rectum. Propranolol absorption from Witespol and macrogol suppositories with lauric acid at a 1:1 molar ratio was much larger than that after propranolol alone. The results supported the concept that a portion of propranolol, by forming a 1:1 complex with lauric acid, would penetrate across the rectal mucosa more easily than propranolol alone.

In an article in Pharm. Res. (1989), 6(7), 628–632 by P G Green et al, it is disclosed that the lipophilicity of cationic drugs can be increased by forming ion pairs with the carboxylate anion of fatty acids. Transport of cations across an iso-Pr myristate membrane was facilitated in the presence of oleic acid, and lauric acid, providing an appropriate pH gradient existed.

Slowly dissolving albuterol salts prepared with adipic and stearic acids have been investigated as a potential means of extending the duration of action of the drug following aerosol delivery to the lung [Jashnani, R et al, J. Pharm. Sci. 1993, 82(6), 613–16.].

From the above prior art it is evident that enhancement of penetration of active agents through the skin, intestinal, oral, nasal or rectal mucosa has been effected by incorporation of fatty acids or bile acids present as the free acid or usually as the sodium salt at a given concentration in a pharmaceutical composition containing an active agent, present as free acid or free base, or as a simple pharmaceutically acceptable salt. Little attention has been paid to means of manipulating the active agents per se to attain enhanced penetration through the membrane barrier.

Cyclodextrins and their derivatives have found extensive application as solubilizers and stabilizers due to their ability to form inclusion complexes with a wide variety of compounds [see (J Szejtli, Cyclodextrin Technology, Kluwer Academic Press) and (J Szejtli & K-H Fromming, Cyclodextrins in Pharmacy, Kluwer Academic Press)]. Cyclodextrins have been used to enhance intestinal absorption of drugs primarily through increasing solubility. Recently, cyclodextrins have been shown to have positive and negative effects on transdermal penetration of drugs [see (Loftsson, T et al, International Journal of Pharmaceutics 1995, 115, 255–258), (Vollmer, U et al, International Journal of Pharmaceutics 1993, 99, 51–58), (Legendre, J Y et al, European Journal of Pharmaceutical Sciences 1995, 3, 311–322) and (Vollmer, U et al, Journal of Pharmacy and Pharmacology 1994, 46, 19–22)]. Cyclodextrins may improve nasal absorption of drugs [see (Merkus, F W et al, Pharmaceutical Research 1991, 8, 588–592) and (Shao, Z et al, Pharmaceutical Research 1992, 9, 1157–1163)] and enhance absorption from sublingual administration of drug/cyclodextrin complexes [Behrouz, S et al, Journal of Clinical Endocrinology and Metabolism 1995, 80, 3567–3575]. Cyclodextrins also protect nasal mucosal damage by penetration enhancers [see Jabbal-Gill, I et al, European Journal of Pharmaceutical Sciences 1994, 1(5), 229–236].

Cyclodextrins are water soluble cone-shaped cyclic oligosaccharides containing 6, 7 or 8 glucopyranose units. The interior or "cavity" of the cone is hydrophobic whilst the exterior is hydrophilic. The size of the cavity increases with increasing number of glucose units. Several cyclodextrin derivatives such as alkyl, hydroxyalkyl and sulfoalkyl ethers have been prepared with improved solubility [see (J Szejtli & K-H Fromming, Cyclodextrins in Pharmacy, Kluwer Academic Press) and (Stella, V J et al, Pharmaceutical Research 1995, 12 (9) S205)].

SUMMARY OF THE INVENTION

According to a first aspect of the invention there is provided a pharmaceutical composition formulated for transdermal or transmucosal delivery comprising as an active ingredient a compound of the formula I:

$B^+RCOO^-$ wherein $B^+$ is a cation of a basic drug, and $RCOO^-$ is an anion of a bile acid, together with one or more excipients for transdermal or transmucosal delivery.

According to a second aspect of the invention there is provided a compound of the formula I:

$B^+RCOO^-$ wherein $B^+$ is a cation of a basic drug and $RCOO^-$ an anion of a bile acid.

According to a third aspect of the invention there is provided the use of a compound of the formula I:

$B^+RCOO^-$ wherein $B^+$ is a cation of a basic drug, and $RCOO^-$ is an anion of a bile acid, together with one or more excipients for transdermal or transmucosal delivery, in the manufacture of a medicament for transmucosal or transdermal delivery.

According to a fourth aspect of the invention there is provided a pharmaceutical composition formulated for transdermal or transmucosal delivery comprising as an active ingredient a compound selected from the group consisting of sumatriptan caprate, sumatriptan laurate, sumatriptan glycodeoxycholate, salbutamol laurate, salbutamol caprate, salbutarnol glycodeoxycholate, codeine caprate, codeine laurate, loperamide glycodeoxycholate, sumatriptan caprate cyclodextrin complex, salbutamol caprate cyclodextrin complex, and salbutamol glycodeoxycholate cyclodextrin complex, together with one or more excipients for transdermal or transmucosal delivery.

DESCRIPTION OF EMBODIMENTS

The first aspect of the invention is a pharmaceutical composition formulated for transdermal or preferably transmucosal delivery comprising as an active ingredient a compound of the formula I:

$B^+RCCO^-$ wherein $B^+$ is a cation of a basic drug, and $RCOO^-$ is an anion of a bile acid, together with one or more excipients for transdermal or transmucosal delivery.

By a "basic drug" there is meant a drug which contains one or more protonable functionalities. Suitable drugs are set out in the Table below. Those marked with an * are preferred.

| CLASS | EXAMPLES |
|---|---|
| Analgesics (opioids) and derivatives | codeine*<br>morphine*<br><br>benzylmorphine<br>propoxyphene<br>methadone<br>pentazocine<br>sufenatanil<br>alfentanil<br>fentanyl*<br>pethidine<br>butorphanol<br>buprenorphine<br>diamorphine<br>dihydrocodeine<br>dypyrone<br>oxycodone<br>dipipanone<br>alphaprodine |

| CLASS | EXAMPLES |
|---|---|
| | levorphanol |
| | dextromoramide |
| | hydromorphone |
| | nalbuphine |
| | oxymorphone |
| | hydrocodone |
| | (nalorphine - antagonist) |
| | (naloxone - antagonist) |
| Antimicrobials | |
| Quinolones | norfloxacin |
| | ciprofloxacin |
| | lomefloxacin |
| | balofloxacin |
| | ofloxacin |
| | sparfloxacin |
| | tosufloxacin |
| | temafloxacin |
| | clinafloxacin |
| | perfloxacin |
| | tosufloxacin |
| | enoxacin |
| | amifloxacin |
| | fleroxacin |
| Aminoglycosides | streptomycin |
| | amikacin |
| | gentamicin |
| | tobramycin |
| | neomycin |
| | josamycin |
| | spectinomycin |
| | kanamycin |
| | framycetin |
| | paromomycin |
| | sissomycin |
| | viomycin |
| Glycopeptides | vancomycin |
| Lincosamides | clindamycin |
| | lincomycin |
| Penicillins, cephalosporins and related β-lactams | cefepime |
| | cefmenoxime |
| | cefotiam |
| | cephalexin |
| | bacampicillin |
| | lenampicillin |
| | pivampicillin |
| | talampicillin |
| Macrolides | erythromycin |
| | oleandomycin |
| Tetracyclines | tetracycline |
| | minocycline |
| | rolitetracycline |
| | methacycline |
| | meclocycline |
| Antimycobacterials | isoniazid |
| | pyrimethamine |
| | ethambutol |
| Antivirals | acyclovir |
| | saquinavir |
| | indinavir |
| | ganciclovir |
| | amantadine |
| | moroxydine |
| | rimantidine |
| | famciclovir |
| | zalcitabine |
| | cidofovir |
| | valacyclovir |
| | lamivudine |
| | nevirapine |
| Antiprotozoals | metronidazole |
| | temidazole |
| | pentamidine |
| | mepacrine |
| | carnidazole |
| | robenidine |
| | emetine |

| CLASS | EXAMPLES |
|---|---|
| | dihydroemetine |
| | halofuginone |
| | homidium |
| | melarsoprol |
| Antiseptics | aminacrine |
| Antifungals | ketoconazole |
| | itraconazole |
| | miconazole |
| | econazole |
| | clotrimazole |
| | amphotericin B |
| | butoconazole |
| | chlormidazole |
| | croconazole |
| | diamthazole |
| | fenticonazole |
| | nystatin |
| | cloconazole |
| | econazole |
| | miconazole |
| | tioconazole |
| Anti-depressants (all classes) | clomipramine |
| | lofepramine |
| | phenelzine |
| | tranylcypromine |
| | dothiepin |
| | nortryptaline |
| | amitryptaline |
| | imipramine |
| | mianserin |
| | maprotiline |
| | desipramine |
| | trazodone |
| | fluoxetine |
| | trimipramine |
| | citalopram |
| | doxepin |
| | fluvoxamine |
| | lofepramine |
| | nomifensine |
| | paroxetine |
| Anti-diabetics | glipizide |
| | metformin |
| | phenformin |
| Anti-convulsants | carbamazepine |
| | ethosuxamide |
| | diphenylhydantoin |
| | phenytoin(–OH) |
| | primidone |
| | methsuximide |
| Anticholinergics (antimuscarinics) (all classes) | atropine |
| | benztropine |
| | scopolamine |
| | homatropine |
| | hyoscine |
| | hyoscyamine |
| | orphenadrine |
| | pirenzipine |
| | procyclidine |
| | telenzipine |
| | propantheline |
| | dicyclomine |
| | biperiden |
| | trihexphenidyl |
| | oxybutinin |
| | benzhexol |
| | biperiden |
| | ipratropium |
| | pipenzolate |
| | mepenzolate |
| | cyclopentolate |

-continued

| CLASS | EXAMPLES |
|---|---|
| Anthelminitics | albendazole |
| | mebendazole |
| | flubendazole |
| | fenbendazole |
| | pyrantel |
| | ivermectin |
| Antigout | allopurinol |
| | colchicine |
| Antihistamines and phenothiazines (all classes) | chlorpheniramine |
| | dimenhydrinate |
| | hydroxyzine |
| | diphenhydramine |
| | bromodiphenhydramine |
| | astemizole |
| | loratidine |
| | acepromazine |
| | thioridazine |
| | brompheniramine |
| | carbinoxamine |
| | chlorcyclizine |
| | chloropyramine |
| | chlorphentermine |
| | chlorprothixene |
| | dexchlorpheniramine |
| | antazoline |
| | azatidine |
| | azalastine |
| | clemastine |
| | clemizole |
| | cyroheptadine |
| | diphenylpyraline |
| | doxylamine |
| | flunarizine |
| | mequitazine |
| | meclozine |
| | mepyramine |
| | pheniramine |
| | terfenadine |
| | triprolidine |
| | trimeprazine |
| | ebastine |
| | cinnarizine |
| Anti-migraines | ergotamine |
| | dihydroergotamine |
| | methysergide |
| | sumatriptan* |
| | naritriptan |
| | almotriptan |
| | zolmitriptan* |
| | rizatriptan* |
| | eletriptan |
| | flumedroxone |
| | pizotifen |
| Anti-tussives and mucolytics | dextromethorphan |
| | pholcodeine |
| | acetylcysteine |
| | noscapine |
| Antineoplastics and Immunosupressants | azathiprine |
| | methyluracil |
| | fluorouracil |
| | vincristine |
| | vinblastine |
| | melphalan |
| | cyclophosphamide |
| | aminoglutethimide |
| | mercaptopurine |
| | tamoxifen |
| | chlorambucil |
| | daunorubicin |
| | mechlorethamine |
| | doxorubicin |

-continued

| CLASS | EXAMPLES |
|---|---|
| Anti-malarials | quinine |
| | chloroquine |
| | pyrimethamine |
| | amodiaquine |
| | piperaquine |
| | proguanil |
| | chloroproguanil |
| | mefloquine |
| | primaquine |
| | halofantrine |
| Anxiolytics, Sedatives, Hypnotics, Antipsycotics | bromazepam |
| | nitrazepam |
| | diazepam |
| | oxazepam |
| Benzodiazepines | clonazepam |
| | chlorazepate |
| | lorazepam |
| | midazolam |
| | triazolam |
| | flunitrazepam |
| Butyrophenones | droperidol |
| | haloperidol |
| Barbiturates | allobarbitone |
| | aprobarbitone |
| | phenobarbitone |
| | amylobarbitone |
| | barbitone |
| | butobarbitone |
| Other | zopiclone |
| | hydroxyzine |
| | buspirone |
| | tandospirone |
| Bronchodilators (other) | theophylline |
| Cardiovascular Drugs | |
| | acebutatol |
| a) β-Blockers | alprenolol |
| | atenolol |
| | labetalol |
| | metopralol |
| | nadolol |
| | timolol |
| | propanolol |
| | pindolol |
| | tolamolol |
| | sotalol |
| | oxprenolol |
| | bunitrolol |
| | carazolol |
| | indenolol |
| b) Anti-arrythmics/ cardiotonics | disopyramide |
| | mexilitine |
| | tocainide |
| | aprindine |
| | procainamide |
| | quinidine |
| | dobutamine |
| c) Ca channel blockers (all classes) | verapamil* |
| | diltiazem |
| | amlodipine |
| | felodipine |
| | nicardipine* |
| | gallopamil |
| | prenylamine |
| c) Antihypertensives/ Vasodilators clonidine | diazoxide |
| | guanethidine |
| | hydralizine |
| | dihydralizine |
| | minoxidil |
| | prazosin |
| | phenoxybenzamine |
| | reserpine |
| | phentolamine |

-continued

| CLASS | EXAMPLES |
|---|---|
| | perhexiline |
| | indapamide |
| | debrisoquine |
| | bamethan |
| | bethanidine |
| | dobutamine |
| | indoramin |
| d) Ace inhibitors | captopril* |
| | enalapril* |
| | lisinopril |
| | ramipril* |
| | imidapril |
| CNS stimulants/ anorectics | methylphenidate |
| | fenfluramine |
| | |
| | amphetamine |
| | methamphetamine |
| | bemegride |
| | caffeine |
| | dexamphetamine |
| | chlorphentamine |
| | fencamfamine |
| | prolintane |
| Diuretics | furosemide |
| | |
| | acetazolamide |
| | amiloride |
| | triampterene |
| | bendrofluazide |
| | chlorothiazide |
| | chlorthalidone |
| | cyclothiazide |
| | hydroflumethiazide |
| | hydrochlorothiazide |
| | hydroflumethiazide |
| Gatrointestinal Agents | |
| a) Motility enhancers, modulators and anti-emetics | domperidone |
| | metoclopramide* |
| | cisapride |
| | prochlorperazine |
| | pirenzipine |
| | cinitapride |
| | cyclizine* |
| | chlorpromazine |
| | prochloperazine |
| | promethazine |
| c) Acid secretion modulators | cimetidine |
| | ranitidine |
| | famotidine |
| | omeprazole |
| | nizatidine |
| d) Anti-diarrhoels | loperamide* |
| | diphenoxylate* |
| e) Emetics | apomorphine |
| Muscle relaxants | chlorzoxazon |
| | |
| | rocuronium |
| | suxamethonium |
| | vecuronium |
| | atracurium |
| | fazadinium |
| | doxacurium |
| | mivacurium |
| | pancuronium |
| | tubocurarine |
| | pipecurium |
| | decamethonium |
| | tizanidine |
| | piridinol |
| | succinylcholine |
| Cholinergic Agents | acetylcholine |
| | |
| | benzpyrinium |
| | edrophonium |
| | physostigmine |

-continued

| CLASS | EXAMPLES |
|---|---|
| | neostigmine |
| | pyridostygmine |
| β-adrenergic agonists | adrenaline |
| | |
| | ephedrine |
| | pseudo-ephedrine |
| | amidephrine |
| | oxymetazoline |
| | xylometazoline |
| | terbutaline* |
| | salbutamol* |
| | salmeterol* |
| | phenylpropanolamine |
| | cyclopentamine |
| | phenylephrine |
| | isoproterenol |
| | fenoterol* |
| | xamoterol |
| Other CNS active agents | dopamine |
| | |
| | levodopa |
| Endocrine agents | bromocriptine |
| | |
| | propylthiouracil |
| Local anaesthetics | lidocaine (lignocaine)* |
| | |
| | procaine* |
| | amethocaine |
| | bupivacaine* |
| | butacaine |
| | oxybuprocaine |
| | mepivacaine |
| | cocaine |
| | prilocaine |
| | amylocaine |
| | chloroprocaine |
| | cinchocaine |
| | etidocaine |
| | propoxycaine |
| | tropacocaine |
| Miscellaneous | |
| Mydriatics | cyclopentolate |
| Antiglaucoma | methazolamide |
| | dorzolamide |
| | acetazolamide |
| Opioid peptides | dynorphins* |
| | enkephalins |
| Peptides | oxytocin |
| | vasopressin |

Preferred drugs include sumatriptan, salbutamol (also known as albuterol), codeine, and loperamide.

The invention also includes a pharmaceutical composition formulated for transdermal or transmucosal delivery comprising as an active ingredient a compound selected from the group consisting of sumatriptan caprate, sumatriptan laurate, sumatriptan glycodeoxycholate, salbutamol laurate, salbutamol caprate, salbutamol glycodeoxycholate, codeine caprate, codeine laurate, loperamide glycodeoxycholate, sumatriptan caprate cyclodextrin complex, salbutamol caprate cyclodextrin complex, and salbutamol glycodeoxycholate cyclodextrin complex, together with one or more excipients for transdermal or transmucosal delivery.

The monocarboxylic fatty acids for use in the present invention, namely $C_{10}$—capric acid $CH_3(CH_2)_8COOH$; and
$C_{12}$—lauric acid $CH_3(CH_2)_{10}COOH$ may be manufactured from fats and oils derived from edible sources which are approved by the Food and Drug Administration (CFR 21 172.860).

The bile acids include all monobasic carboxylic acids derived from bile and include: glycocholic acid, glycodeoxycholic acid, cholic acid, deoxycholic acid, taurocholic acid, and taurodexycholic acid.

The preferred anions for use with the preferred basic drugs listed above are glycodeoxycholate anions.

In terms of the invention, an acid addition salt in solid, isolated form, is formed between the cation of the basic drug and the anion of the fatty acid or bile acid.

The fatty acids and bile acids are known as penetration enhancers, i.e compounds which alter the membrane as a barrier or otherwise increase the flux of a desired drug across the barrier. The formation of these acid addition salts enhances the transmucosal and transdermal penetration of the basic drugs.

By the terms "mucosal" or "mucosa" or "mucosae" is meant the epithelial membranes lining the oral, nasal, rectal, vaginal and ocular cavities.

By the term "dermal" or "skin" is meant any skin surface.

The fatty acid and bile acid addition salts of pharmaceutically active agents or drugs according to the invention are characterised by a relatively low aqueous solubility. The salts may be prepared by any conventional means such as dissolving the free base of the drug in a suitable solvent such as a lower alcohol, preferably methanol or ethanol previously dehydrated to give a half saturated solution, to which is added 1 mol equivalent of either fatty or bile acid with stirring. The resulting solution may be heated to between 40–60° C. for one to several hours. The solvent is removed by rotary evaporation under vacuum and dried at elevated temperature in vacuo to constant weight. Alternatively, the sodium salt of the fatty acid or bile acid is dissolved in water at elevated temperature. A solution of the commercially available salt of the drug (e.g hydrochloride, sulphate, succinate, phosphate, etc) is added slowly with stirring at elevated temperature. The resulting solution is cooled to room temperature and the addition salt precipitate collected on a filter, washed with cold water and dried in vacuo.

The aqueous solubility of the fatty acid or bile acid addition salt of the drug may be increased by complexation with a cyclodextrin. The cyclodextrin may be α, β or γ-cyclodextrin or derivative thereof. Cyclodextrin inclusion complexes may be prepared on the basis of liquid state, solid state or semi-solid state reaction between the components (J Szeitli, Cyclodextrin Technology, Kluwer Academic Press). The inclusion complex may be prepared by conventional means such as kneading 1:1 mol/mol quantities of the salt and cyclodextrin in the presence of a small amount of water to produce a uniform paste. The mixture is vigorously kneaded for 0.25–4 hours and then dried under vacuum at elevated temperature. The product obtained is characterised by an increase in drug water solubility at 25° C. relative to the free uncomplexed acid addition salt.

A preferred pharmaceutical composition of the invention is a sublingual tablet containing a therapeutic dose of a basic drug in the form of a fatty acid or bile acid addition salt present as a cyclodextrin inclusion complex capable of rapid dissolution. Preferred compounds for sublingual administration include drugs from therapeutic categories where rapid therapeutic response is required or where limitations are imposed by conventional delivery (analgesics, antimigraine, anti-emetic, anxiolytics, anti-diarreals, anti-arrythmics, anti-hypertensives, anti-anginals, anti-asthmatics, hormones, peptide-based pharmaceuticals). The composition may contain additional permeation enhancers such as laurocapram or sodium dodecyl sulphate. Conventional excipients such as binders (microcrystalline cellulose), disintegrants (sodium carboxymethyl cellulose), buffers (tromethamine, sodium bicarbonate, sodium carbonate) flavours, lubricants (magnesium stearate, sodium stearyl fumarate) and organopletic modifying agents (xylitol) may be added in suitable quantities. The excipients with the exception of flavours and lubricant, are granulated together with the complex and dried. The dried granulate is sieved together with the lubricant and flavour and mixed. The mixture is compressed at 20–50N into sublingual tablets.

The acid addition salt present in part or completely as a cyclodextrin inclusion complex may be formulated together with conventional pharmaceutical excipients into sustained release buccal tablets or patches with uni-directional release according to methods known in the art. Preferred excipients for sustained release buccal tablets or patches are muco-adhesive polymers such as cross-linked polyacrylic acids (carbomers, polycarbophils).

The acid addition salt or the water soluble cyclodextrin complex of the acid addition salt may be formulated as drops, spray or gel for buccal or sublingual administration according to methods known in the art. Preferred excipients include viscosity modifying agents (e.g hydroxypropylmethylcellulose, carbomers, polycarbophils, chitosans, guar gum, alginates), flavours, buffers (tromethamine, sodium bicarbonate, sodium carbonate), preservatives (bronopol, benzalkonium chloride, EDTA, chlorhexidine gluconate) and anti-oxidants (N-acetyl-cysteine, sodium sulfite, sodium metabisulfite).

The acid addition salt or the water soluble cyclodextrin inclusion complex of the salt may be formulated as a powder insufflation or for nasal administration according to conventional methods. Preferred excipients include muco-adhesive polymers to enhance residence time (e.g carbomers, polycarbophils, chitosans).

The water soluble cyclodextrin inclusion complex of the salt may be formulated as an aqueous nasal spray according to methods appreciated in the art. Preferred excipients include muco-adhesive polymers to enhance residence time (e.g carbomers, polycarbophils, chitosans), viscosity modifying agents (alkylcelluloses, hydroxyalkylcelluloses, hydroxypropylmethylcellulose, carbomers, polycarbophils, chitosans, guar gum, alginates, buffers (tromethamine, sodium bicarbonate, sodium carbonate), preservatives (bronopol, benzalkonium chloride, EDTA, chlorhexidine gluconate) and anti-oxidants (N-acetyl-cysteine, sodium sulfite, sodium metabisulfite).

The acid addition salt or the water soluble cyclodextrin inclusion complex of the acid addition salt may be formulated for rectal administration as a suppository according to conventional methods.

The acid addition salt or the water soluble cyclodextrin inclusion complex of the acid addition salt may be formulated for vaginal administration as a pessary according to conventional methods.

The acid addition salt may be formulated for ocular administration as an eye ointment according to conventional methods.

The acid addition salt or the water soluble cyclodextrin inclusion complex of the salt may be formulated for ocular administration as eye-drops according to conventional methods.

The general principles of formulation and manufacture of sublingual, buccal, nasal, rectal, vaginal and ocular pharmaceutical compositions may be found in The Pharmaceutical Codex 12th Edition. The Pharmaceutical Press; Remington's Pharmaceutical Sciences 18th Edition, Mack Publishing Company. Transdermal pharmaceutical compositions have been extensively reviewed [Osborne, D. W and Amann, A. topical Drug Delivery Formulations, Marcel Dekker Inc.].

The invention encompasses the use of a broad range of pharmaceutically active agents which are capable of forming acid addition salts with fatty acids or bile acids. The compositions of this invention may be utilized in delivering the pharmaceutically active agent to the following target areas: (1) the sublingual surface or floor of mouth, (2) the buccal cavity, (3) the gums, (4) the nasal passages, (5) the rectum or colon, (6) the vagina, (7) the ocular cavity or cul-de-sac of the eye, and (8) the skin.

The preferred pharmaceutical forms are sublingual tablets, nasal sprays, buccal tablets, suppositories (rectal and vaginal), transdermal patches and topical gels.

Examples of the invention will now be given.

EXAMPLE 1

Sumatriptan base ((2.29g; 7.75 mmol) was dissolved in boiling ethyl acetate (300 mL) with stirring. Capric acid (1.33 g; 7.75 mmol) was dissolved in ethyl acetate (10 mL) and added to the sumatriptan base solution in one portion. The hot solution was stirred for a further 10 minutes and allowed to cool to room temperature. Evaporation of the solvent by rotary evaporation rave a pale yellow oil. Hexane (50 mL) was added and a white precipitate formed that was filtered off under vacuum. The precipitate was washed with hexane and allowed to dry at room temperature to give sumatriptan caprate as a pale yellow solid (2.79 g; 77.4%). The sumatriptan caprate was characterised by DSC and FT-IR. DSC gave a single, sharp endotherm with the onset at 94.6° C. The FT-IR differed significantly from that of the sumatriptan base.

EXAMPLE 2

Salbutamol base (13.91 g; 58.13 mmol) was dissolved in ethanol (600 mL, 96%) with magnetic stirring to give a pale yellow liquid. Capric acid (10.01 g; 58.11 mmol) was added with vigorous stirring which was continued until all solid material had dissolved. The solvent was removed by rotary-evaporation to give a pale yellow tacky semi-solid. This was dissolved in warm ethyl acetate (300 mL), then stored at 5° C. for 36 hours, resulting in the precipitation of a fine white solid. The mother liquor was removed by vacuum filtration, and the precipitate washed with cold ethyl acetate. Any remaining solvent was removed by storing the precipitate at 35° C. and 0 bar pressure for 6 hours. Salbutamol caprate was obtained as a white solid (18.93 g; 79.13%). Moisture content K.F. 0.32%; melting point 99.4° C. (onset of endotherm in DCS thermogram). The theoretical percentage of salbutamol base in salbutamol caprate is 58.14%. Experimentally the percentage salbutamol base in salbutamol caprate was found to be 56.42%. The pH of a saturated aqueous solution is 7.24. The aqueous solubility is 4.76 mg/mL.

EXAMPLE 3

Salbutamol base (4.00 g; 16.72 mmol) was dissolved in ethanol (200 mL; 99.7–100%), to which was added lauric acid (3.681 g; 18.39 mmol; 10% molar excess relative to salbutamol base) and dissolved. A pale yellow solution was formed. Removal of the ethanol by rotary-evaporation gave a viscous, pale yellow residue. The residue was redissolved in ethyl acetate (10 mL) by gentle heating on a water bath (60° C.). The solution was placed in a fridge overnight. A white precipitate formed which was isolated by vacuum filtration and washed with 10 mL cold ethyl acetate. The precipitate was dried further in a vacuum oven at 40° C. for 16 hours. This gave salbutamol laurate as a white powder (6.6461 g; 86.5% yield). Melting point was found to be 104° C. (onset of endotherm in DSC thermogram). Theoretically salbutamol laurate contains 54.43% m/m salbutamol base.

EXAMPLE 4

Salbutamol base (1.2007 g; 5.02 mmol) was dissolved in ethanol (100 mL) with vigorous stirring. Glycodeoxycholic acid (2.4601 g; water content: 4.25% w/w; 5.25 mmol~5% molar excess) was added and dissolved with stirring. A clear, colourless solution was obtained. The ethanol was removed by vacuum rotary-evaporation to give a viscous, yellow residue. Ethyl acetate (200 mL) was added to the residue and the mixture heated in a water bath with constant agitation. As the yellow residue dissolved, a white precipitate formed. Agitation was continued until the yellow residue disappeared. The ethyl acetate solution was cooled in an ice bath. The precipitate was isolated by vacuum filtration and dried in a vacuum oven at 40° C. for 20 hours to give salbutamol glycodeoxycholate (3.662 g; water content; 4.95% w/w; % yield; 97.9%). Analysis by differential scanning calorimetry from 50 to 200° C. gave no significant thermal event. Slow decomposition was evident after 110° C. A saturated aqueous solution gave a pH of 6.12. The aqueous solubility was greater than 8.35 mg/mL. The theoretical percentage of salbutamol base in the salbutamol glycodeoxycholate 34.74%.

EXAMPLE 5

Codeine base (4.0016 g; 12.60 mmol) was dissolved in ethanol (100 ml). Capric acid (2.3902 g; 13.86 mmol) was added and dissolved with stirring. The ethanol was removed under vacuum. The residue was redispersed in ethyl acetate (25 mL) which was then removed under vacuum, and the residue redissolved in ethyl acetate (10 mL) with heating on a water bath (60° C.). The ethyl acetate solution was placed in a fridge for 16 hours to yield a white precipitate which was isolated by vacuum filtration and washed with cold ethyl acetate (20 mL). This precipitate proved to be very deliquescent, and on standing became a viscous, clear mass. This mass was redissolved in ethyl acetate (200 mL), the solvent was evaporated to give a viscous yellow residue. This residue was stored at 8° C. for 48 hours to give a pale yellow solid. This solid was dried under vacuum (0 bar) at 25° C. This yielded codeine caprate as a pale yellow solid (5.7301 g; 89.6% yield). The material was analysed by Differential Scanning Calorimetry in order to determine the melting point. However, thermal analysis from 50 to 200° C. showed no thermal event.

EXAMPLE 6

Codeine base (4.0002 g; 12.60 mmol) was dissolved in ethanol (100 mL; 99.7–100%) with stirring. Lauric acid (2.7822 g; 13.86 mmol; 10% excess relative to codeine base) was dissolved in the ethanol/codeine solution. The resulting solution was stirred for 5 minutes. The ethanol was removed by rotary-evaporation to give a pale yellow residue. The residue was redispersed in ethyl acetate (10 mL) by heating on a water bath (60° C.). Once all the material had redissolved the solution was placed at 4° C. for 16 hours. A white precipitate formed which was isolated by vacuum filtration. The precipitate was dried further in a vacuum oven for 16 hours at 40° C. to give codeine laurate (2.4757 g; 36.50%). The material was analysed by Differential Scanning Calorimetry in order to determine the melting point. However, thermal analysis from 50 to 200° C. showed no thermal event.

EXAMPLE 7

Sodium glycodeoxycholate (0.1211 g;~0.24 mmol) was dissolved in hot (80° C.) deionized water (50 mL). Loperamide HCl was dissolved in hot (80° C.) deionized water (100 mL). The loperamide HCl solution was added dropwise to the sodium glycodeoxycholate solution which stirring at 80° C. Immediately upon addition of the loperamide HCl solution a white precipitate was formed. After addition of the loperamide HCl solution, the resulting suspension was stirred for 5 minutes at 80° C. This suspension was allowed to cool to room temperature, then filtered through filter paper (Whatman No 5) under vacuum. The precipitate was dried further in a vacuum oven at 40° C. for 16 hours. This gave a white powder (0.0771 g; 34.36°). Analysis by Differential Scanning Calorimetry to obtain a melting point yielded no thermal event from 50 to 250° C.

EXAMPLE 8

Sumatriptan caprate and hydroxypropyl-beta cyclodextrin (HPB) were complexed by the kneading method. Sumatriptan caprate (1.254 g) and HPB (3.748 g) were blended together. Water (4.5 mL) was added and the mixture ground together in a mortar with a pestle to form a uniform paste. Grinding was continued for 30 minutes. The paste was then dried in a vacuum oven (40° C.; 0 bar) for 48 hours. The solid mass was broken up, passed through a 60 mesh screen and returned to the vacuum oven (40° C.; 0 bar) for 12 hours in order to ensure uniform drying of the complex. Analysis by HPLC for sumatriptan base content, and Karl Fischer for moisture content gave the following results: % sumatriptan base was 16.40% and the moisture content was 3.45%. The complex was characterised by DSC, FT-IR and XRD.

EXAMPLE 9

Sumatriptan caprate and gamma-cyclodextrin was complexed by the kneading method. Sumatriptan caprate (1.325 g) and gamma-cyclodextrin (3.675 g) were blended together. Water (6 mL) was added and the mixture ground together in a mortar with a pestle to form a uniform paste. Grinding was continued for 30 minutes. The paste was then dried in a vacuum oven (40° C.; 0 bar) for 48 hours. The solid mass was broken up, passed through a 60 mesh screen and returned to the vacuum oven (40° C.; 0 bar) for 12 hours in order to ensure uniform drying of the complex. Analysis by HPLC for sumatriptan base content, and Karl Fischer for moisture content gave the following results: % sumatriptan base was 16.78% and the moisture content was 6.80%. The complex was characterised by DSC, FT-IR and XRD.

EXAMPLE 10

Salbutamol caprate and hydroxypropyl-beta cyclodextrin (HBP) were complexed by the kneading method. Salbutamol caprate (2.72 g) and HPB (7.728 g) were blended together. Water (5 mL) was added and the mixture ground together in a mortar with a pestle to form a uniform paste. Grinding was continued for 30 minutes. The paste was then dried in a vacuum oven (40° C.; 0 bar) for 48 hours. The solid mass was broken up, passed through a 60 mesh screen and returned to the vacuum oven (40° C.; 0 bar) for 12 hours in order to ensure uniform drying of the complex. Analysis of HPLC for salbutamol base content, and Karl Fischer for moisture content gave the following) results: % salbutamol base was 12.97%, and the moisture content was 5.56%. The complex was characterised by DSC, FT-IR and XRD. The solubility in aqueous solution was greater than 4.8 mg/mL, and the pH of a saturated aqueous solution was 6.79.

EXAMPLE 11

Salbutamol caprate and gamma-cyclodextrin were complexed by the kneading method. Salbutamol caprate (2.409 g) and gamma-cyclodextrin (7.591 g) were blended together. Water (12 mL) was added and the mixture ground together in a mortar with a pestle to form a uniform paste. Grinding was continued for 30 minutes. The paste was then dried in a vacuum oven (40° C.; 0 bar) for 48 hours. The solid mass was broken up, passed through a 60 mesh screen and returned to the vacuum oven (40° C.; 0 bar) for 12 hours in order to ensure uniform drying of the complex. Analysis by HPLC for salbutamol base content, and Karl Fischer for moisture content gave the following results: % salbutamol base was 12.83%, and the moisture content was 7.92%. The complex was characterised by DSC, FT-IR and XRD. The solubility in aqueous solution was 3.2 mg/mL, and the pH of a saturated aqueous solution was 7.00.

EXAMPLE 12

Codeine laurate and hydroxypropyl-beta-cyclodextrin were complexed by the kneading method. Codeine laurate (0.700 g) and hydroxypropyl-beta-cyclodextrin (2.045 g) were blended together. Water (5 ml was added and the mixture ground together in a mortar with a pestle to form a uniform paste. Grinding was continued for 30 minutes. The paste was then dried in a vacuum oven (40° C.; 0 bar) for 48 hours. The solid mass was broken up, passed through a 60 mesh screen and returned to the vacuum oven (40° C.; 0 bar) for 12 hours in order to ensure uniform drying of the complex. Analysis by HPLC for codeine base content, and Karl Fisher for moisture content gave the following results: % codeine base was 14.49%, and the moisture contents was 4.21%. The complex was characterised by DSC, FT-IR and XRD.

EXAMPLE 13

Codeine laurate and gamma-cyclodextrin were complexed by the kneading method. Codeine laurate (0.700 g) and gamma-cyclodextrin (1.754 g) were blended together. Water (2.5 mL) was added and the mixture ground together in a mortar with a pestle to form a uniform paste. Grinding was continued for 30 minutes. The paste was then dried in a vacuum oven (40° C.; 0 bar) for 48 hours. The solid mass was broken up, passed through a 60 mesh screen and returned to the vacuum oven (40° C.; 0 bar) for 12 hours in order to ensure uniform drying of the complex. Analysis by HPLC for codeine base content, and Karl Fischer for moisture content gave the following results: % codeine base was 16.08%, and the moisture content was 8.72%. The complex was characterised by DSC, FT-IR and XRD.

EXAMPLE 14

The unit composition of a sublingual tablet containing the equivalent of 4 mg salbutamol base is as follows:

| | |
|---|---|
| Salbutamol caprate gamma-CD complex (for Example 9) | 32 mg |
| Lactose NF | 20 mg |
| Magnesium stearate | 1 mg |

The complex is blended with the lactose. The lubricant is blended and formed into sublingual tablets by compression at 10–30N.

EXAMPLE 15

Codeine laurate hydroxypropyl-beta-cyclodextrin complex from Example 12 (1.352 g equivalent to 200 mg codeine base) is dissolved in purified deionised water (8 ml) buffered to pH 7.4 with phosphate buffer. Chlorhexidine gluconate (0.01%) is added. The volume is adjusted to 10 ml by addition of phosphate buffer pH 7.4 and the tonicity of the final solution is adjusted with sodium chloride to 300 mOsm/kg. The solution is filtered and filled into a metered dose nasal spray bottle. Each 0.25 ml metered dose contains 5 mg codeine base suitable for nasal administration.

EXAMPLE 16

The unit composition of a suppository containing the equivalent of 20 mg sumatriptan base is as follows:

| | |
|---|---|
| Somatriptan caprate | 32 mg |
| Macrogol 6000 | 500 mg |
| Macrogol 1540 | 300 mg |
| Macrogol 400 | 200 mg |

The macrogols ware heated to just above melting point. Finely divided sumatriptan caprate is blended into the melt. The homogeneous liquid mass is poured into a mould.

EXAMPLE 17

Salbutamol laurate from Example 3 (15 mg equivalent to 8 mg salbutamol base) is dissolved 0.5 ml of a mixture of propylene glycol (95%) and laurocapram (5%). The resulting solution is filled into a reservoir transdermal delivery system.

The physichochemical characteristics of several free bases, acid addition salts and their cyclodextrin complexes are tabulated in Table 1. Melting points (peak onset temperature) were determined by Differential Scanning Calorimetry using a Perkin Elmer DSC 7. The saturation solubilities were determined by shaking an excess of the compound in phosphate buffer pH 7.4 at 25° C. The mixture was filtered (0.22(m) and the filtrate analysed by HPLC for drug content. The acid addition salts are less soluble than the corresponding free bases. The solubility of the acid addition salts may be increased by cyclodextrin complexation. Partition coefficients offer a prediction of the tendency for a drug to move from an aqueous compartment into a membrane, and consequently have been found to correlate well with biological response [Pharmaceutical Codex 12th Edition, Pharmaceutical Press p 188]. In order to show that the acid addition salts possess improved membrane partitioning properties relative to the corresponding free bases, the apparent partition coefficients (Papp) were determined according to the following method [Pharmaceutical Codex 12 Edition. Pharmaceutical Press p70]:

$$Papp = P/(1+10^{pKa-pH})$$

where $P = C_o/C_w$ and where $C_o$ is the concentration of the drug in n-octanol and $C_w$ is the concentration of the drug in phosphate buffer pH 7.4 at 25° C. Drug concentrations were determined by HPLC.

An increase in the apparent partition coefficient of the acid addition salt relative to the corresponding free base is indicative of increased lipophilicity which is related to rate of transfer of a molecule across a biological membrane. The results in Table 1 clearly illustrate that the acid addition salts of the invention possess higher apparent partition coefficients relative to the corresponding free bases.

TABLE 1

MELTING POINTS AND EQUILIBRIUM SOLUBILITY DATA ON ACID ADDITION SALTS

| Compound | Melting Point (° C.) | Equilibrium solubility (mg/ml) |
|---|---|---|
| Sumatriptan base | 169,0 | 2,342 |
| Sumatriptan caprate | 94,6 | 3,849 |
| Salbutamol base | 148,8 | 16,663 |
| Salbutamol caprate | 99,4 | 3,820 |
| Salbutamol laurate | 104,0 | 4,245 |
| Salbutamol glycodeoxycholate | Does not melt below 200 | 12,363 |
| Codeine base | 152.7 | 10,574 |
| Codeine laurate | Does not melt below 200 | 5,227 |
| Sumatriptan caprate HPBCD | 88,8 | 4,333 |
| Sumatriptan caprate GDC | 86,8 | 3,250 |
| Salbutamol caprate HPBCD | 91,0 | 4,107 |
| Salbutamol caprate GCD | Does not melt below 200 | 1,865 |
| Codeine laurate HPBCD | Does not melt below 200 | 4,263 |
| Codeine laurate GCD | Does not melt below 200 | 1,353 |

Melting point is given as onset value from DSC. If there is no endotherm then it is recorded as "does not melt below . . ." maximum temperature of DSC run. Equilibrium solubility in phosphate buffer pH 7.4 (low ionic strength) at 25° C.

TABLE 2

PARTITION COEFFICIENTS AND APPARENT PARTITION COEFFICIENTS FOR ACID ADDITION SALTS

| Compound | Partition Coefficient | Apparent Partition Coefficient |
|---|---|---|
| Sumatriptan base | 0,69 | 0,004039 |
| Sumatriptan caprate | 1,54 | 0.009015 |
| Salbutamol base | 0,42 | 0.005222 |
| Salbutamol caprate | 0,54 | 0,006714 |
| Salbutamol glycodeoxycholate | 0,61 | 0,007584 |

Apparent partition coefficient in phosphate buffer pH 7.4 and n-octanol at 25° C.

What is claimed is:

1. A compound of formula I:

$B^+RCOO^-$ wherein $B^+$ is a cation of a basic drug and $RCOO^-$ is an anion of a bile acid, in solid isolated form.

2. A compound according to claim 1, where $B^+$ is a cation of a basic drug selected from the group consisting of codeine, morphine, fentanyl, naratriptan, zolmitriptan, rizatriptan, verapamil, nicardipine, captopril, enalapril, ramipril, metoclopramide, cyclizine, diphenoxylate, salmeterol, fenoterol, terbutaline, bupivacaine, lidocaine, procaine and dynorphin.

3. A compound according to claim 1, wherein $B^+$ is a cation of a basic drug selected from the group consisting of sumatriptan, salbutamol, codeine and loperamide.

4. A compound according to any one of the claims 1 to 3, wherein $RCOO^-$ is glycodeoxycholate.

5. A cyclodextrin inclusion complex comprises a compound of the formula I:

$B^+RCCO^-$ wherein B⁺ is a cation of a basic drug and RCOO⁻ is an anion of a bile acid, and an unsubstituted or substituted α, β or γ-cyclodextrin.

6. A pharmaceutical composition formulated for transdermal or transmucosal delivery comprising as an active ingredient a compound of formula I:

B⁺RCOO⁻ wherein B⁺ is a cation of a basic drug and RCOO⁻ is an anion of a bile acid, the active ingredient being in solid, isolated form, together with one or more excipients for transdermal or transmucosal delivery.

7. A pharmaceutical composition formulated for transdermal or transmucosal delivery comprising as an active ingredient a compound of formula I:

B⁺RCOO⁻ wherein B⁺ is a cation of a basic drug and RCOO⁻ is an anion of a bile acid, the active ingredient being in the form of a cyclodextrin inclusion complex, together with one or more excipients for transdermal or transmucosal delivery.

8. A pharmaceutical composition according to claim 6 or 7, wherein B⁺ is a cation of a basic drug selected from the group consisting of codeine, morphine, fentanyl, naratriptan, zolmitriptan, rizatriptan, verapamil, nicardipine, captopril, enalapril, ramipril, metoclopramide, cyclizine, diphenoxylate, salmeterol, fenoterol, terbutaline, bupivacaine, lidocaine, procaine and dynorphin.

9. A pharmaceutical composition according to claim 6 or 7 wherein B⁺ is a cation of a basic drug selected from the group consisting of sumatriptan, salbutamol, codeine and loperamide.

10. A pharmaceutical composition according to claims 6 to 7, wherein RCOO⁻ is glycodeoxycholate.

11. A pharmaceutical composition formulated for transdermal or transmucosal delivery comprising as an active ingredient a compound selected from the group consisting of sumatriptan caprate, sumatriptan laurate, sumatriptan glycodeoxycholate, salbutamol laurate, salbutamol caprate, salbutamol glycodeoxycholate, codeine caprate, codeine laurate, loperamide glycodeoxycholate, sumatriptan caprate cyclodextrin complex, salbutamol caprate cyclodextrin complex, and salbutamol glycodeoxycholate cyclodextrin complex, together with one or more excipients for transdermal or transmucosal delivery.

12. A pharmaceutical composition according to claims 6 to 7, selected from the group consisting of a sublingual tablet, a nasal spray, a buccal tablet and a suppository.

13. A pharmaceutical composition according to claims 6 to 7, selected from the group consisting of a transdermal patch and a topical gel.

* * * * *